United States Patent [19]
Hirota et al.

[11] Patent Number: 5,302,550

[45] Date of Patent: * Apr. 12, 1994

[54] METHOD OF BONDING A MICROELECTRONIC DEVICE

[75] Inventors: Jitsuho Hirota; Kazumichi Machida, both of Amagasaki; Masaaki Shimotomai; Seizo Omae, both of Itami, all of Japan

[73] Assignee: Mitsubishi Denki Kabushiki Kaisha, Tokyo, Japan

[*] Notice: The portion of the term of this patent subsequent to Oct. 12, 2008 has been disclaimed.

[21] Appl. No.: 223,980

[22] Filed: Apr. 13, 1988

Related U.S. Application Data

[63] Continuation-in-part of Ser. No. 944,213, Dec. 22, 1986, which is a continuation-in-part of Ser. No. 938,515, Dec. 5, 1986.

[30] Foreign Application Priority Data

Dec. 24, 1985 [JP] Japan ................................. 60-291082
Dec. 24, 1985 [JP] Japan ................................. 60-291084
Jan. 28, 1986 [JP] Japan ................................. 61-17348
Jan. 28, 1986 [JP] Japan ................................. 61-17349

[51] Int. Cl.$^5$ ........................................ H01L 21/607
[52] U.S. Cl. ........................................ 437/194; 437/183; 228/1.1; 228/4.5; 219/56.22; 219/86.61; 257/746
[58] Field of Search ............... 437/194, 183, 174; 219/56.22, 86.61; 357/67; 228/1.1, 4.5

[56] References Cited

U.S. PATENT DOCUMENTS

4,732,313  3/1988  Kobayashi et al. .................. 228/4.5

FOREIGN PATENT DOCUMENTS

0169574  1/1986  European Pat. Off. .

OTHER PUBLICATIONS

"Copper bonding could outshine gold", C. Cohen, Electronics, Jul. 25, 1985, pp. 27-28.
"Ultrasonic Hardness Testing", G. Kossoff et al., Ultrasonics, Apr. 1968, pp. 88-91.
Johnson et al. "Development of Aluminum Ball/Wedge Wire Welding" Int. J. Hybrid Microelectron, vol. 4, No. 1, Spring 1981.

Primary Examiner—Brian E. Hearn
Assistant Examiner—Tuan Nguyen
Attorney, Agent, or Firm—Sterne, Kessler, Goldstein & Fox

[57] ABSTRACT

A method for ball-bonding thin film structures. The bonding characteristics of a thin-film electrode structure are measured, before the actual bonding step, by pressing a ball (of a material similar to that of the bonding wire) against an electrode by a bonding capillary, and then measuring the resultant indentation of the electrode. The depth of this test indentation of the electrode has a good correlation with the bondability.

15 Claims, 6 Drawing Sheets

METHOD OF BONDING A MICROELECTRONIC DEVICE

CROSS-REFERENCE TO RELATED APPLICATIONS

The present application is a continuation-in-part of Ser. No. 944,213, filed Dec. 22, 1986, and also of Ser. No. 938,515. Through those applications, priority under §119 is claimed, based on Japanese applications 291082/85 (filed Dec. 24, 1985), 17349/86 (filed Jan. 28, 1986), 291084/85 (filed Dec. 24, 1985), and 17348/86 (filed Jan. 28, 1986).

BACKGROUND OF THE INVENTION

The present invention relates to a method of manufacturing a semiconductor device, such as an IC (integrated circuit) or a discrete semiconductor device having an electrode thereon connected to a lead, and to semiconductor devices provided by implementation of the method.

FIG. 1 shows a method of wire bonding on such a semiconductor device. This wire bonding step serves to connect an aluminum electrode 3 (formed on a semiconductor chip 2) to a lead 4, using a gold capillary wire 1 which is supplied through a bonding tool 5. The lead 4 would typically be of a copper alloy which has received a surface treatment, such as plating with silver or the like.

To accomplish such a connection, an end of the gold wire 1 is made to melt by means of arc heat input, and is then solidified to form a ball 1a. Then the ball 1a is ball-bonded to the aluminum electrode (FIGS. 1a and 1b). After that, the wire 1 is led off and stitch-bonded to the lead 4 (FIGS. 1c and 1d). The thermosonic method is often employed for the bonding of the wire 1.

Since gold wire is expensive, and the long-term reliability of the junction between gold wire and the aluminum electrode is not sufficiently high, various alternative materials and bonding techniques have been studied.

One candidate to substitute for gold is copper, since copper is less expensive and offers good long-term reliability. A problem associated with copper is inferior bondability of copper wire to an aluminum electrode. If the power of the ultrasonic wave is increased in an attempt to assist the bond, aluminum may be driven outward, as indicated by reference numeral 3a in FIG. 2, so that the ball 10a of the copper wire 10 may abut the semiconductor chip 2. Thus, the electrode 3 and the semiconductor chip 2 may be damaged.

When this problem occurs, various known measures may be taken. For instance, the quality of the aluminum may be adjusted. But in view of the fact that the semiconductor devices are mostly mass-produced, it is necessary to be able to assess the bondability of the aluminum electrode film in order to maintain the desired quality without having bonding-related failures occur in manufactured product.

Conventionally, accurate assessment of the bondability requires various tests. These tests would include, e.g., a test of the bond strength, and observation of how the alloy layer is formed and how the aluminum film is deformed and driven away. (Such observations can be made by looking at the cross section of the bonded part.) The bond strength can be measured by measuring the shear strength of the bonded part. Typically, 40 grams-force (0.39 Newton) or more is a required level of the breaking load. For assessment of the electrode for the purpose of quality control during mass-production, a simpler test method is desired.

One known method of assessment of aluminum from the viewpoint of bondability is to measure the hardness (Knoop hardness). But this measurement is conducted under a situation different from the actual bonding. Moveover, the error of the measurement for a very light load is considerable. A very light load must be used for testing because the load under bonding is very light, and the measurement differs depending on the magnitude of the load.

Additional background information on conventional bonding methods may be found in U.S. Pat. No. 4,705,204; Kurtz, "Copper wire Ball Bonding," 34th ECC Proceedings (1984) at pages 1–6; and Onuki et al., "Study of Aluminum Ball Bonding for Semiconductors," 34th ECC Proceedings (1984) at pages 7–12; and in references cited in these publications; all of which are hereby incorporated by reference.

SUMMARY OF THE INVENTION

An advantage of the innovative teachings set forth herein is that an improved bond is achieved between the electrode of a semiconductor chip and a bonding wire.

Another advantage of the innovative teachings set forth herein is that the danger of damage during bonding to the semiconductor chip and the electrode is minimized.

Another advantage of the innovative teachings set forth herein is that the danger of damage to the semiconductor chip and the electrode is minimized.

The present inventors have found that, if a ball of a material similar to the bonding wire is pressed against an electrode by a bonding capillary, the depth of the resultant indentation of the electrode has a good correlation with the bondability.

The present inventors have also found that a good bond can be obtained, even with low ultrasonic power, if the quality of the electrode film is adjusted properly. The electrode characteristics are controlled so that the depth of a test indentation, which results when a ball of material identical or similar to the material of the bonding wire is pressed against the electrode under certain conditions, is within a certain range.

An advantage of the present invention is that assessment of the electrode characteristics, for the purpose of quality control during mass-production, can be achieved using a simple test method. The innovations described herein obviate the need to resort to complicated and time consuming procedures, as has hitherto been required.

Another advantage of the invention is to provide a more accurate method of assessment of thin-film electrode structures.

In particular, one class of embodiments permits ball bonding with copper wire. In this class of embodiments, a test is performed using a copper ball. After the bonding capillary has pressed the copper ball against the electrode, the resulting test indentation is measured. The depth of this indentation provides a way to assess the index of bondability of the electrode very accurately.

According to one aspect of the invention, there is provided: A method of manufacturing a semiconductor device having an electrode on which a bonding wire is to be bonded, comprising the steps of: preparing a semiconductor structure having a thin film electrode thereon; wherein preparation of said semiconductor structure is controlled so that said electrode has mechanical qualities such that the depth of a test indentation, which results when a ball of a material identical or similar to the material of said bonding wire is pressed against a specimen of said electrode, is within a certain range; and bonding said bonding wire to said electrode.

According to another aspect of the invention, there is provided: A semiconductor chip produced by a process comprising the steps of: providing a semiconductor structure including at least one thin film electrode portion on which a bonding wire is to be connected; pressing a ball, of a material identical or similar to the material of the bonding wire, against a specimen of said thin film electrode to produce a test indentation; measuring the depth of said test indentation; and controlling the characteristics of said thin film electrode with respect to said test indentation measurement, so that said test indentation depth measurements fall within a certain range.

According to another aspect of the invention, there is provided: A method of assessing the bondability of an electrode film of a semiconductor device on which a bonding wire is to be bonded, comprising the steps of: pressing a ball of a material similar in mechanical properties to the material of the bonding wire, using a bonding capillary, against the electrode film to produce a test indentation; and measuring the depth of the indentation of the electrode film due to said pressing step.

BRIEF DESCRIPTION OF THE DRAWING

The present invention will be described with reference to the accompanying drawings, which show important sample embodiments of the invention and which are incorporated in the specification hereof by reference, wherein.

DESCRIPTION OF THE PREFERRED EMBODIMENTS

Figure 1:
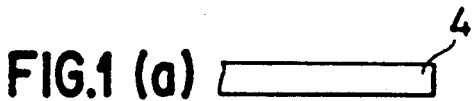
FIGS. 1(a), 1(b), 1(c), 1(d) show schematically how the wire bonding is conducted.
Figure 1:
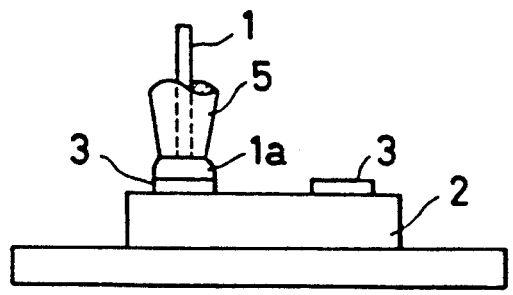
Figure 1:
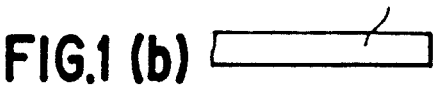
Figure 1:
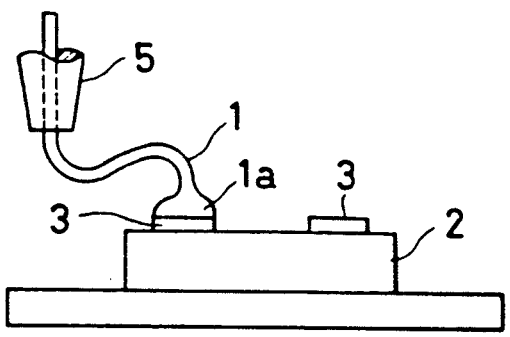
Figure 1:
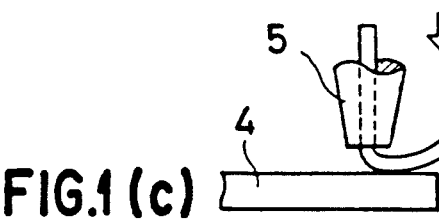
Figure 1:
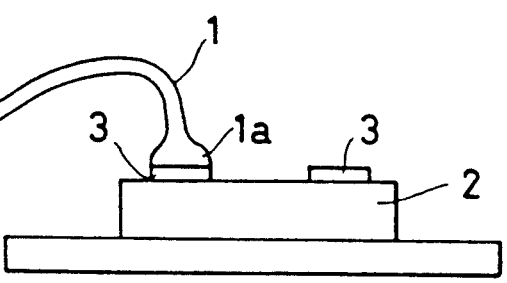
Figure 1:
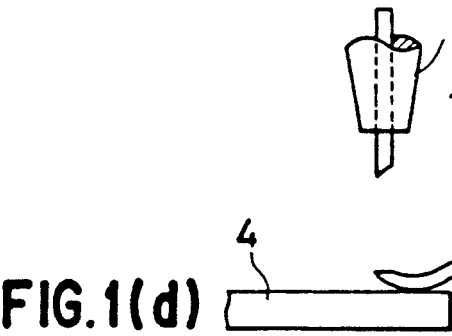
Figure 1:
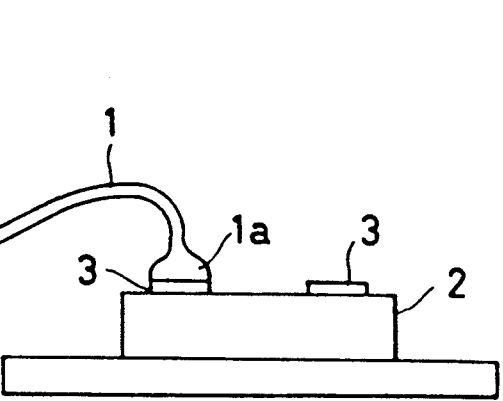
Figure 2:
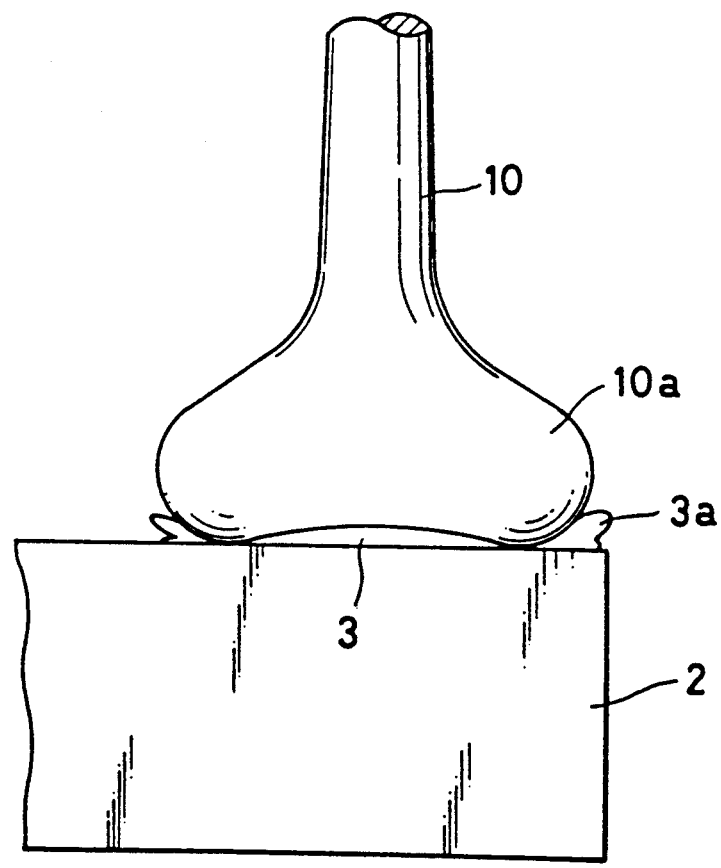
FIG. 2 shows deformation of an electrode film.
Figure 3:
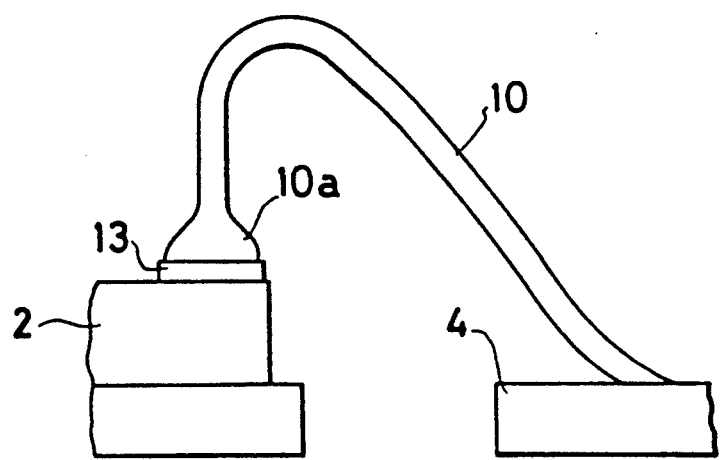
FIG. 3 is a partial elevation showing a semiconductor device having an electrode connected by a bonding wire to a lead.
Figure 4:
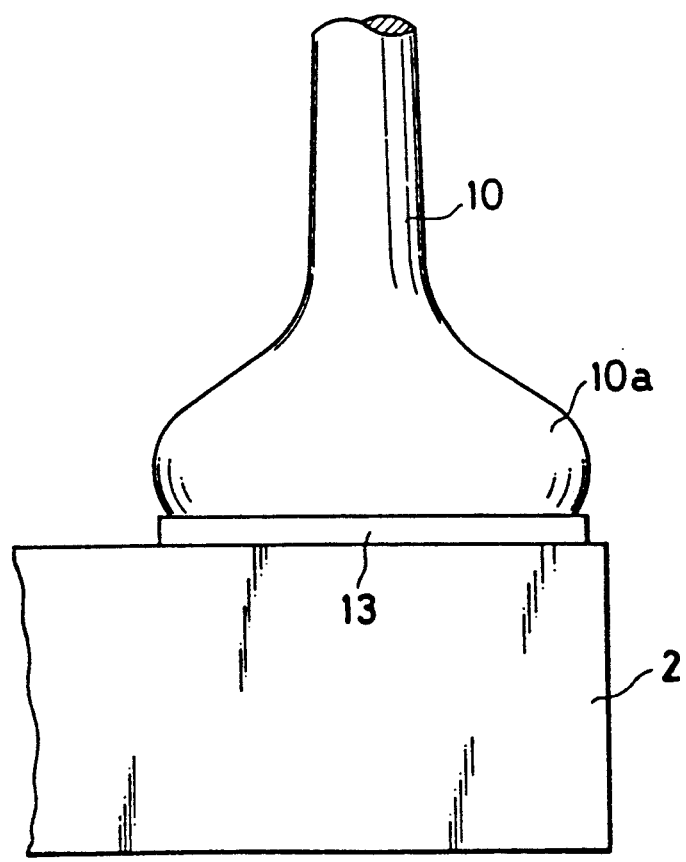
FIG. 4 is an enlarged view showing a ball bonded to an electrode.

FIGS. 3 and 4 show a semiconductor device of an embodiment of the invention. In FIGS. 3 and 4, reference numerals identical to those in FIG. 1 and FIG. 2 denote identical or similar members.

The present invention has been enabled by the discovery that, if a ball of material identical or similar to the material of the bonding wire is pressed against an electrode, the depth of the resultant indentation of the electrode has a good correlation with the bondability. Therefore, if an electrode is formed to have such a quality that the test indentation depth (which results when a ball of a material identical or similar to the material of the bonding wire 1 is pressed against the electrode 3 under certain conditions) is within a certain range, a good bond can be reliably obtained by subsequent bonding.

Figure 5B:
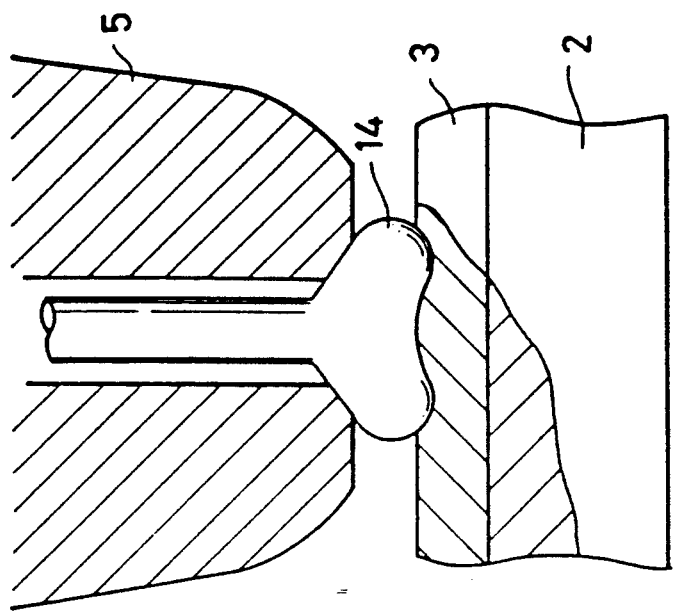
FIGS. 5(a), 5(b) show how a ball is pressed against an electrode film, during assessment of the electrode film.
Figure 5A:
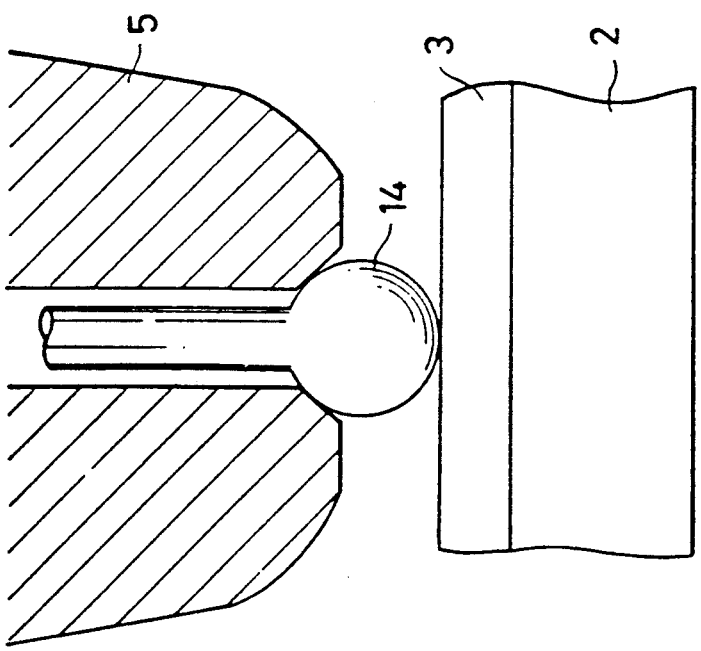

That is, the bondability of the film is assessed from the depth D of a test indentation. For example, a ball 14 of a material identical or similar to that of a bond wire is pressed, using a tool 5, against a thin electrode film 3 on a semiconductor chip 2 (FIG. 5). The amount of the resultant deformation, i.e. the depth D of the resultant indentation (FIG. 6), is measured.

Figure 6:
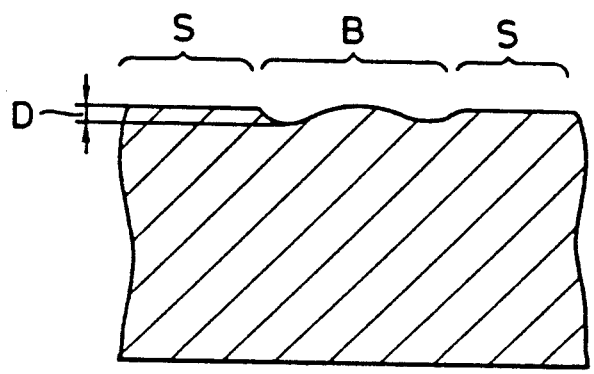
FIG. 6 shows in cross section part of the electrode film which has been indented.

The depth of the test indentation can be measured by observing, by means of a microscope, the cross section shown in FIG. 6 formed by grinding the part B of the electrode to be bonded. The difference in height, as observed through the microscope, between the indented portion B, and the surrounding portions S, i.e., the part which is not to be bonded, is the depth D of the test indentation.

Figure 7:
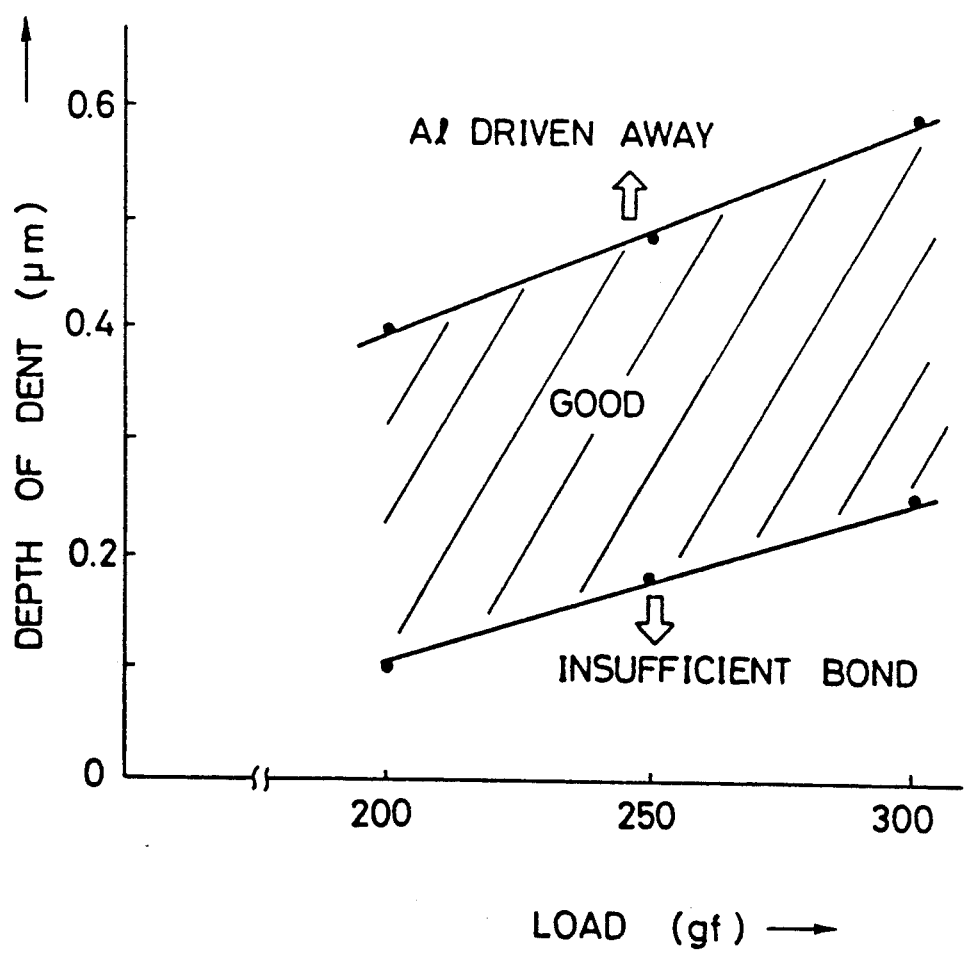
FIG. 7 shows a range of satisfactory conditions in terms of load and the depth of the test indentation.

As an example, it has been found that if a pure copper ball 14 of a diameter of 70 to 75 microns is pressed with a force of 200 to 300 grams-force (2-3 Newtons) against an electrode 3, and the depth of the resultant indentation is within the range of 0.1 to 0.6 microns, then the copper wire 10 can be bonded well to the electrode 3. This is illustrated in FIG. 7, in which the conditions to provide good bondability are indicated. Accordingly, if the measured depth of the test indentation is within the range of 0.1 to 0.6 microns (depending on the applied force), the bondability of the film may be considered acceptable. If the measured depth is outside the range, the bondability is considered unacceptable.

The exact composition and thickness of the electrode 3 are not particularly critical. For example, electrode 3 could be (for example) aluminum doped with 1%-2% silicon, and might be about a micron thick (or slightly less). (However, it is somewhat preferable that the electrode 3 should not be less than 0.8 microns thick.)

If the bondability is found to be unacceptable, various well-known measures can be taken to change the qualities of the aluminum film of the semiconductor devices being mass-produced, so that the semiconductor devices which will next be produced will have an aluminum film of a good bondability. For example, the qualities of the aluminum film may be changed by the conditions of deposition of the aluminum, e.g. the deposition rate and the degree of vacuum. If, for example, the deposition rate is lowered, the aluminum film becomes harder, and the aluminum film becomes more difficult to deform.

Another measure which can be taken, as an alternative to or in addition to the above-mentioned measure, is to change the conditions of a process step carried out after the bonding. For instance, the conditions of sintering the bonding interfaces may be changed to compensate for the deviation in the bondability, so as to optimize the state of the bonded parts.

The following publications (and references cited therein) include some information which may help to show the state of knowledge among those skilled in the art as to how metal deposition or post-processing steps may be varied to change the properties of the resulting metal thin films: Hong et al., "A process dependent study of Al/Si/Cu very large integration metallization (I)," 5 *J. Vac. Sci. Tech. B* 1639 (2nd series)(1987); Holland et al., "Hillock Reduction in Ion-Implanted Metal," 134 *J. Electrochem. Soc.* 2017 (1987); Levy et al., "LPCVD of Tungsten and Aluminum for VLSI Applications," 134 *J. Electrochem. Soc.* 37C (1987); Levy et al., "In-Source Al-0.5%Cu Metallization for CMOS Devices," 132 *J. Electrochem. Soc.* 159 (1985); and Levy et al., "Characterization of LPCVD Aluminum for VLSI Processing," 131 *J. Electrochem. Soc.* 2175 (1984); all of which are hereby incorporated by reference. Of course, depending on the particular metal system being used, a wide variety of specific sources may be consulted.

The novel assessment capability provided herewith also provides a new way to define the characteristics of a semiconductor chip. According to a first embodiment of the invention, a semiconductor chip 2 with an electrode of a thin film having such a quality that the depth of a test indentation which results when a ball of copper of a diameter of 70 to 75 microns is pressed against the electrode with a pressing force of 200 to 300 grams-force (2-3N), is within the range of 0.1 to 0.6 microns, is prepared.

To obtain such a semiconductor chip, the following procedure is followed: First, the conditions under which the electrode 13 is formed are varied until the optimum conditions are found under which the electrode 13 of the desired quality (as defined by a deformation test like that described) is produced. That is, conditions are varied until the depth of the test indentation, which results from pressing a copper ball against an electrode test structure under certain conditions, is within a certain range.

The optimum conditions thus found are fixed or set, and used for the subsequent production of the electrode films on the semiconductor chips. That is, once the conditions for production of the electrode are determined, the electrodes of the semiconductor chip subsequently fabricated are produced under the thus-determined conditions.

The ensuing steps, which make the actual bond connections, may then be identical to those of a conventional method. That is, a ball 10a of copper wire 10 is ball-bonded, with an ultrasonic wave being applied, to the electrode 13 of the semiconductor chip 2, and the copper wire is stitch-bonded to the lead 4.

When copper wire is ball-bonded to an electrode whose quality is controlled as described above, a good bond can be obtained with a low ultrasonic power (i.e. a high ultrasonic power is not needed). The aluminum electrode material is not driven away, so damage to the electrode or the semiconductor chip is prevented. Use of copper wire is thus enabled, and the long-term reliability of the junction between the wire and the electrode is improved.

In another embodiment of the invention, ultrasonic power is applied to the copper ball, while the copper ball is pressed against the electrode test structure. (This embodiment may give more accurate results if ultrasonic power will be applied during the actual bonding steps in production.) Where ultrasonic power is applied, the applied pressure may be reduced. For instance, it has been found that: after a pure copper ball of a diameter of 70 to 75 microns has been pressed against an electrode with an applied force of about 150 grams-force (1.5N) while an ultrasonic wave having an amplitude of 0.07 to 0.14 microns is applied at a frequency of 60 kHz at a temperature of 350° C.; if the depth of the resultant indentation is within the range of 0.1 to 0.6 microns, then the copper wire 10 can be bonded well to the electrode 3.

Figure 8:
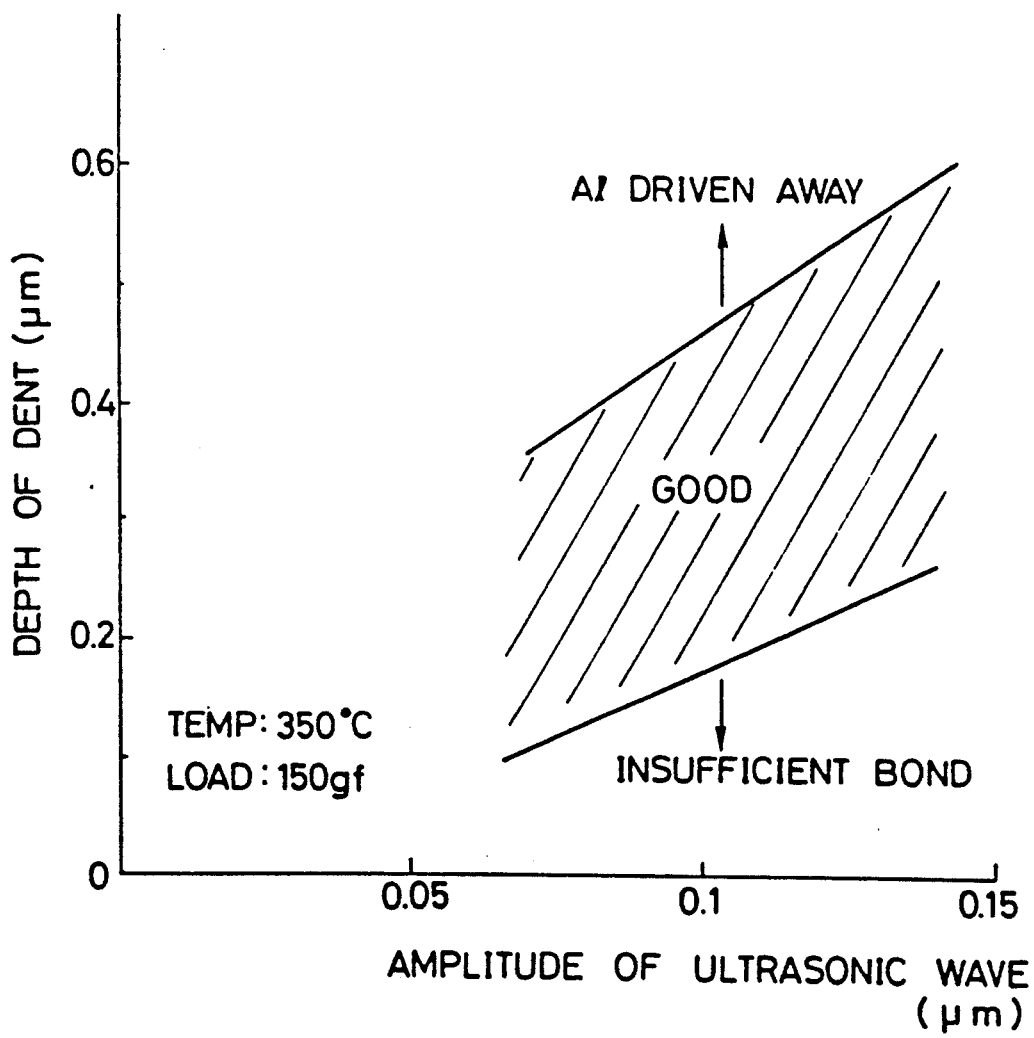
FIG. 8 shows a range of satisfactory conditions in terms of the amplitude of the ultrasonic wave and the depth of the test indentation.

This is illustrated in FIG. 8, in which the hatched region represents the range of conditions in which good bondability is obtained. Accordingly, if the measured depth of the test indentation is within the range of 0.1 to 0.6 microns, the bondability may be considered acceptable. If the measured depth is outside the range, the bondability is considered unacceptable.

If the bondability is unacceptable, measures similar to those described in connection with the first-mentioned embodiment can be taken.

According to another embodiment of the invention, a semiconductor chip 2 with an electrode of a thin film having such a quality that the depth of a test indentation which results when a ball of copper of a diameter of 70 to 75 microns is pressed against the electrode at a temperature of 350° C., with a pressing force of 150 grams-force, with ultrasonic wave of 60 kHz having an amplitude of 0.07 to 0.14 microns being applied, is within 0.1 to 0.6 microns, is prepared. The rest of the procedure is similar to that described with reference to the first embodiment.

In place of the copper wire as used in the above-described embodiments, a wire of a copper alloy (or of other materials) may be used.

Thus, according to the present invention, the bondability is assessed or monitored and controlled in a simple way, so that an electrode film with a good bondability is secured.

The present invention also provides the advantage that the measurement is conducted under conditions similar to those under which the actual bonding is conducted. The assessment is therefore accurate and reliable.

As will be recognized by those skilled in the art, the innovative concepts described in the present application can be modified and varied over a tremendous range of applications, and accordingly their scope is not limited except by the allowed claims.

What is claimed is:

1. A method of manufacturing a semiconductor device having an electrode on which a bonding wire is to be bonded, comprising the steps of:
    preparing a semiconductor structure having electrode film thereon;
    wherein preparation of said semiconductor structure is controlled so that said electrode film has mechanical qualities such that the depth of a test indentation, which results when a ball of a material identical or similar to the material of said bonding wire is pressed against a specimen of said electrode film with a force of about 200 to 300 grams-force, is within the range of 0.1 to 0.6 microns;
    said ball having a diameter of about 70 to 75 microns; and
    bonding said bonding wire to said electrode film.

2. A method according to claim 1, wherein ultrasonic power is applied to said ball while said test indentation is being formed.

3. A method according to claim 1, wherein said electrode film consists essentially of aluminum.

4. A method according to claim 1, wherein said bonding wire is formed of a material selected from the group consisting of: copper and copper alloys.

5. A method according to claim 1, wherein said electrode film consists essentially of aluminum, said bonding wire is formed of a material selected from the group consisting of copper and copper alloys, and said ball is formed of copper.

6. A method according to claim 1, wherein ultrasonic power is applied during said bonding step.

7. A method according to claim 1, wherein said ball is pressed using a bonding capillary to produce said test indentation.

8. A method of manufacturing a semiconductor device having an electrode on which a bonding wire is to be bonded, comprising the steps of:
preparing a semiconductor structure having electrode film thereon;
controlling the preparation of said semiconductor structure so that said electrode film consists essentially of aluminum, and has mechanical qualities such that the depth of a test indentation, which results when a ball having a diameter of about 70 to 75 microns is pressed against a specimen of said electrode film, is within the range of 0.1 to 0.6 microns;
forming said bonding wire of a material selected from the group consisting of copper and copper alloys,
forming said ball of copper,
pressing said ball at a temperature of about 350° C. with a force of about 150 grams-force, and
applying an ultrasonic wave of about 60 kHz having an amplitude of 0.07 to 0.14 microns to produce said test indentation; and
bonding said bonding via wire to said electrode film.

9. A method of assessing the bondability of an electrode film of a semiconductor device on which a bonding wire is to be bonded, comprising the steps of:
pressing a ball of a material similar in mechanical properties to the material of the bonding wire with a force of about 200 to 300 grams-force, using a bonding capillary, against the electrode film to produce a test indentation;
said ball having a diameter of about 70 to 75 microns; and
measuring the depth of the indentation of the electrode film due to said pressing step to determine whether the depth of the test indentation is within the range of 0.1 to 0.6 microns.

10. A method according to claim 9, wherein ultrasonic power is applied to said ball during said pressing step.

11. A method according to claim 9, wherein the electrode film consists essentially of aluminum.

12. A method according to claim 9, wherein the bonding wire is formed of copper or copper alloy.

13. A method according to claim 9, wherein the electrode film consists essentially of aluminum, the bonding wire is formed of copper or copper alloy, and the ball is formed of copper.

14. A method according to claim 13, wherein an ultrasonic wave of about 60 kHz having an amplitude of 0.07 to 0.14 microns is applied.

15. The method of claim 9, wherein said ball consists essentially of material identical to the material of the bonding wire.

* * * * *